US011553910B1

(12) United States Patent
Sartawi

(10) Patent No.: US 11,553,910 B1
(45) Date of Patent: Jan. 17, 2023

(54) MODIFIED INTERVASTUS ARTHROTOMY CLOSURE METHOD

(71) Applicant: GIFTEDNESS AND CREATIVITY COMPANY, Safat (KW)

(72) Inventor: Muthana M. M. A. S. Sartawi, Safat (KW)

(73) Assignee: GIFTEDNESS AND CREATIVITY COMPANY, Safat (KW)

( * ) Notice: Subject to any disclaimer, the term of this patent is extended or adjusted under 35 U.S.C. 154(b) by 0 days.

(21) Appl. No.: 17/668,276

(22) Filed: Feb. 9, 2022

(51) Int. Cl.
*A61B 17/06* (2006.01)

(52) U.S. Cl.
CPC .................................... *A61B 17/06* (2013.01)

(58) Field of Classification Search
CPC ... A61B 17/56; A61B 2017/564; A61B 17/04; A61B 17/06; A61B 17/06004; A61B 17/06066; A61B 17/06109; A61B 2017/06009–06057; A61B 2017/06071–06104; A61F 2/38; A61F 2/461
See application file for complete search history.

(56) References Cited

U.S. PATENT DOCUMENTS

| 10,149,774 | B1 | 12/2018 | Sartawi | |
|---|---|---|---|---|
| 2006/0079852 | A1* | 4/2006 | Bubb | A61M 1/73 604/317 |

FOREIGN PATENT DOCUMENTS

RU 2479273 4/2013

OTHER PUBLICATIONS

Malhotra R, Jain V, Kumar V, Gautam D. Evaluation of running knotless barbed suture for capsular closure in primary total knee arthroplasty for osteoarthritis—a prospective randomized study. Int Orthop. Oct. 2017;41(10):2061-2066. doi: 10.1007/s00264-017-3529-8. Epub Jun. 21, 2017. PMID: 28639008. (Year: 2017).*
Sartawi et al., "Modified Intervastus Approach to the Knee," J Knee Surg., May 2018;31(5):422-424.
Sartawi et al., "A Retrospective Analysis of the Modified Intervastus Approach," Am J Orthop (Belle Mead NJ), Dec. 2018;47(12).
Kobayashi et al., "The effects of barbed suture on watertightness after knee arthrotomy closure: a cadaveric study," J Orthop Surg Res, 13, 323 (2018).

* cited by examiner

*Primary Examiner* — Katherine H Schwiker
(74) *Attorney, Agent, or Firm* — Nath, Goldberg & Meyer; Richard C. Litman

(57) ABSTRACT

A method for arthrotomy closure includes using a first sutured needle to form a first series of parallel stitches from a caudal end of the arthrotomy incision to a first point spaced from the cephalad end of the arthrotomy incision, using a second sutured needle to form a second series of parallel stitches from a cephalad end of the arthrotomy incision to the caudal end of the arthrotomy incision. The second series of stitches intersect the first series of stitches at a 45 degree angle after passing the first point. After the second series of stitches is formed, the first sutured needle is used to form a third series of stitches from the first point to the cephalad end of the arthrotomy incision. The third series of stitches are parallel to the first series of stitches and intersect the second series of stitches at a 45 degree angle.

11 Claims, 7 Drawing Sheets

MODIFIED INTERVASTUS ARTHROTOMY CLOSURE METHOD

BACKGROUND

1. Field

The present subject matter relates generally to surgical procedures and particularly to a modified intervastus (MIV) arthrotomy closure technique.

2. Description of the Related Art

During a total knee arthroplasty, an orthopedic surgeon removes diseased portions of bone in order to shape the remaining bone to accommodate a knee implant. During the procedure, the surgeon builds the artificial knee inside of the patient's leg, one component at a time, to create a highly realistic artificial joint. Although a wide variety of initial procedures exist for gaining access to the bone, each has its own difficulties and potentials for complications.

Of the arthroplasty approaches, the modified intervastus approach (described in U.S. Pat. No. 10,149,774 B1) better preserves the extensor mechanism, is easily extensile, and easy to perform. The method of performing a modified intervastus approach in total knee arthroplasty procedures is an approach in which the arthrotomy is performed with elevation of the vastus medialis off of the underlying capsule. Initially, a straight incision is made that is just medial to the midline, in line with the medial border of the tibial tubercle distally extending just proximal to the patella. This exposes the vastus medialis muscle and the interval between the quadriceps tendon and vastus medialis is then identified.

As this approach is relatively new, however, a suitable technique for arthrotomy closure which provides a watertight seal has not previously been described.

Thus, a method for arthrotomy closure solving the aforementioned problems is desired.

SUMMARY

A method for arthrotomy closure includes using a first sutured needle to form a first series of parallel stitches from a caudal end of the arthrotomy incision to a first point spaced from the cephalad end of the arthrotomy incision, using a second sutured needle to form a second series of parallel stitches from a cephalad end of the arthrotomy incision to the caudal end of the arthrotomy incision. The second series of stitches intersect the first series of stitches (preferably at an angle of 45 degrees) after passing the first point. After the second series of stitches is formed, the first sutured needle is used to form a third series of stitches from the first point to the cephalad end of the arthrotomy incision. The third series of stitches are parallel to the first series of stitches and intersect the second series of stitches (preferably at an angle of 45 degrees). Preferably, a space of 3 mm is provided between adjacent stitches.

These and other features of the present disclosure will become readily apparent upon further review of the following specification and drawings.

DETAILED DESCRIPTION OF THE PREFERRED EMBODIMENTS

Figure 1:
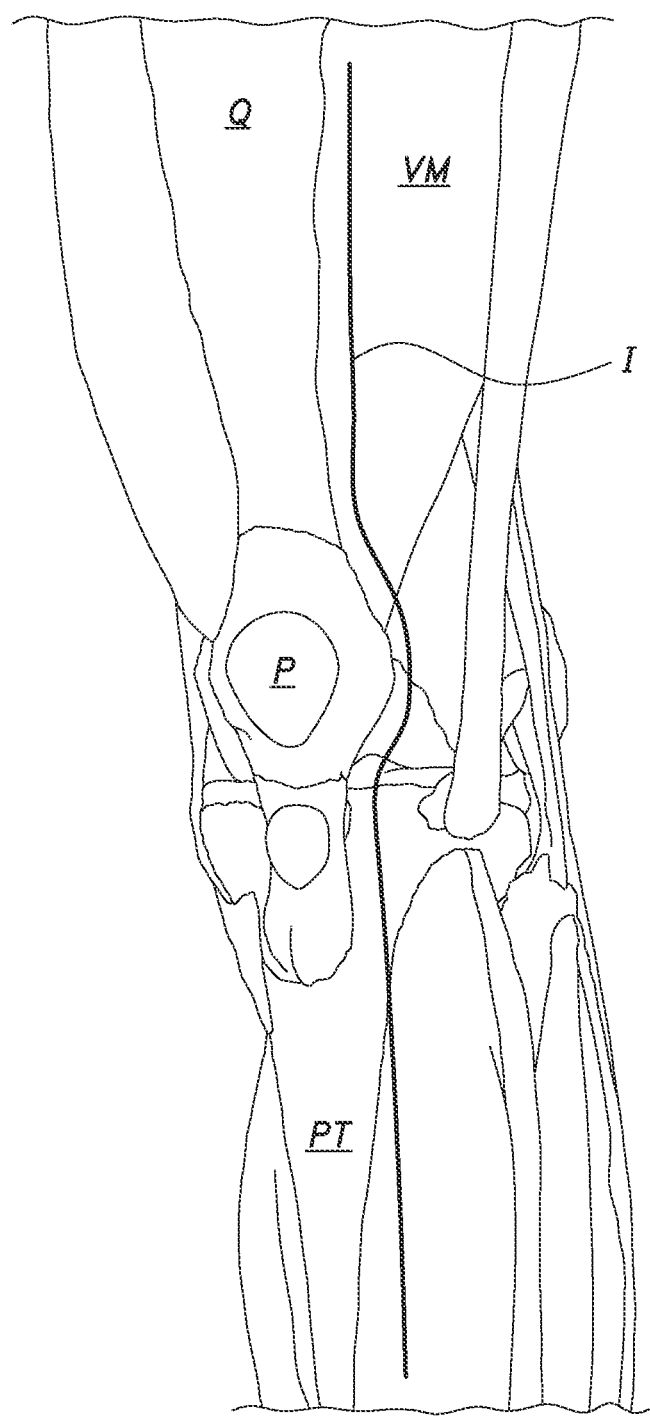
FIG. 1 depicts an exemplary arthrotomy incision.
Figure 2:
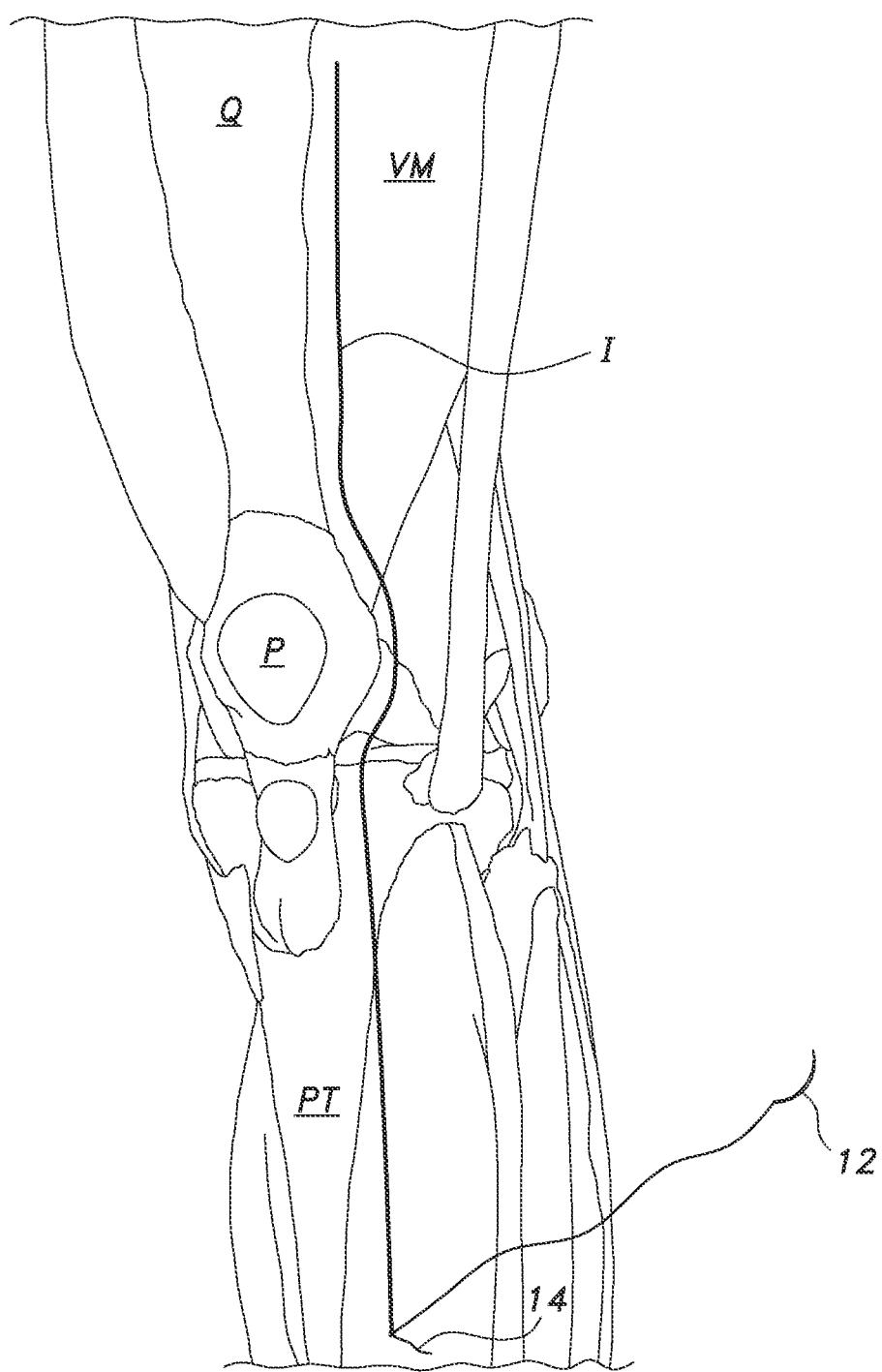
FIG. 2 depicts forming a first stitch in the first series of parallel stitches at a caudal end of the arthrotomy incision according to the present teachings.
Figure 3:
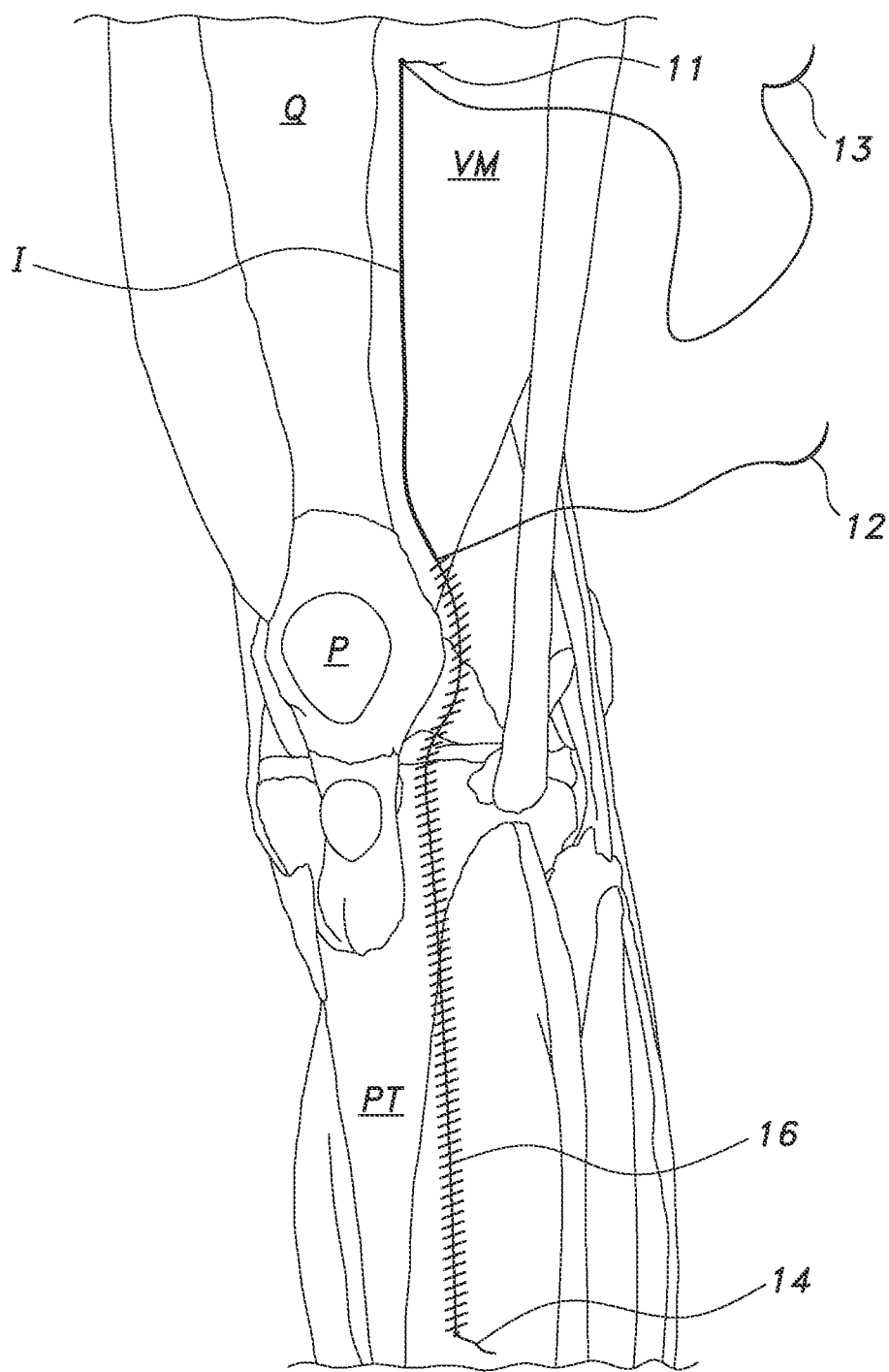
FIG. 3 depicts forming the first series of parallel stitches to a first point.
Figure 4:
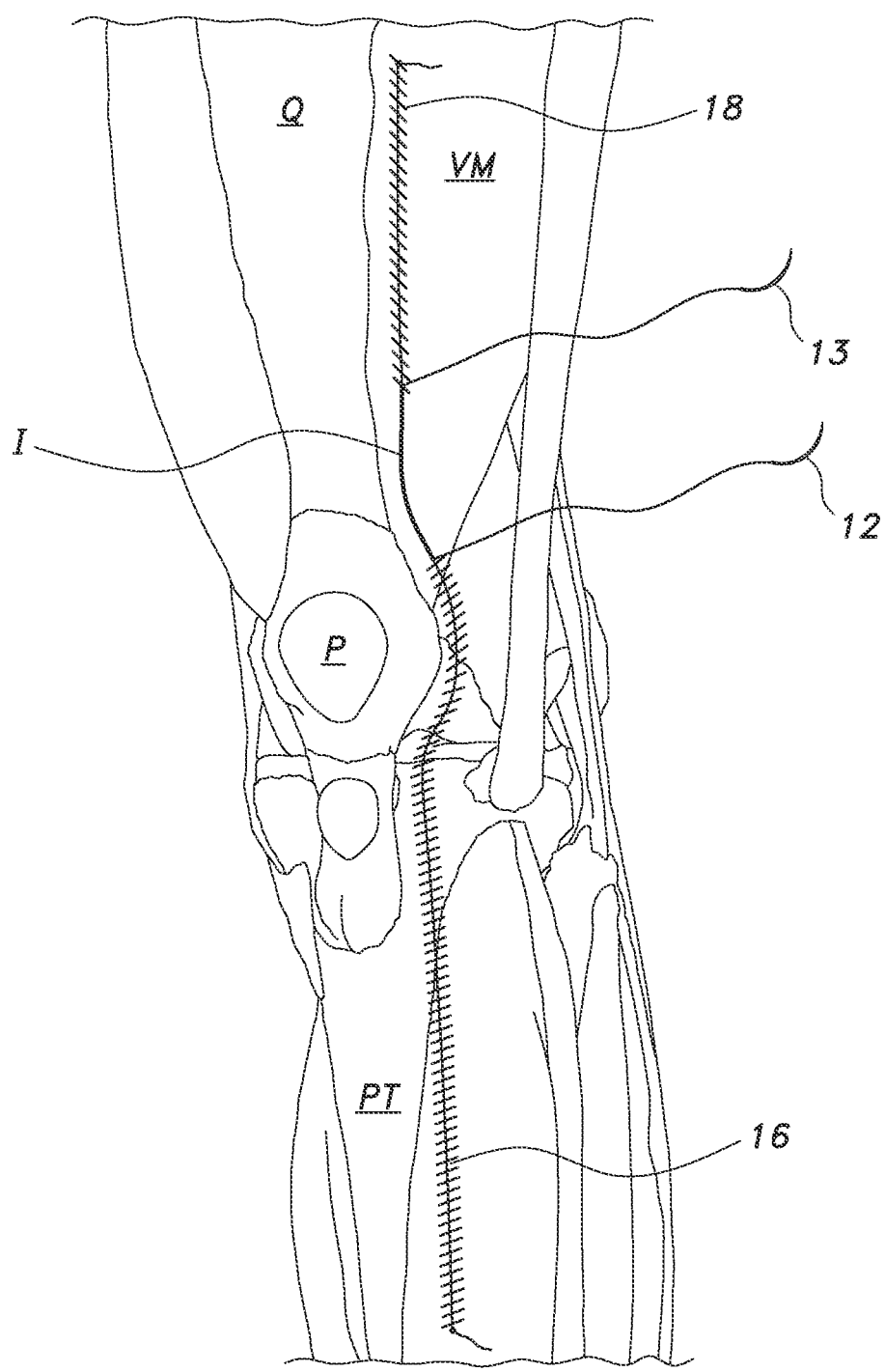
FIG. 4 depicts forming the second series of parallel stitches beginning from a cephalad end of the arthrotomy incision.
Figure 5:
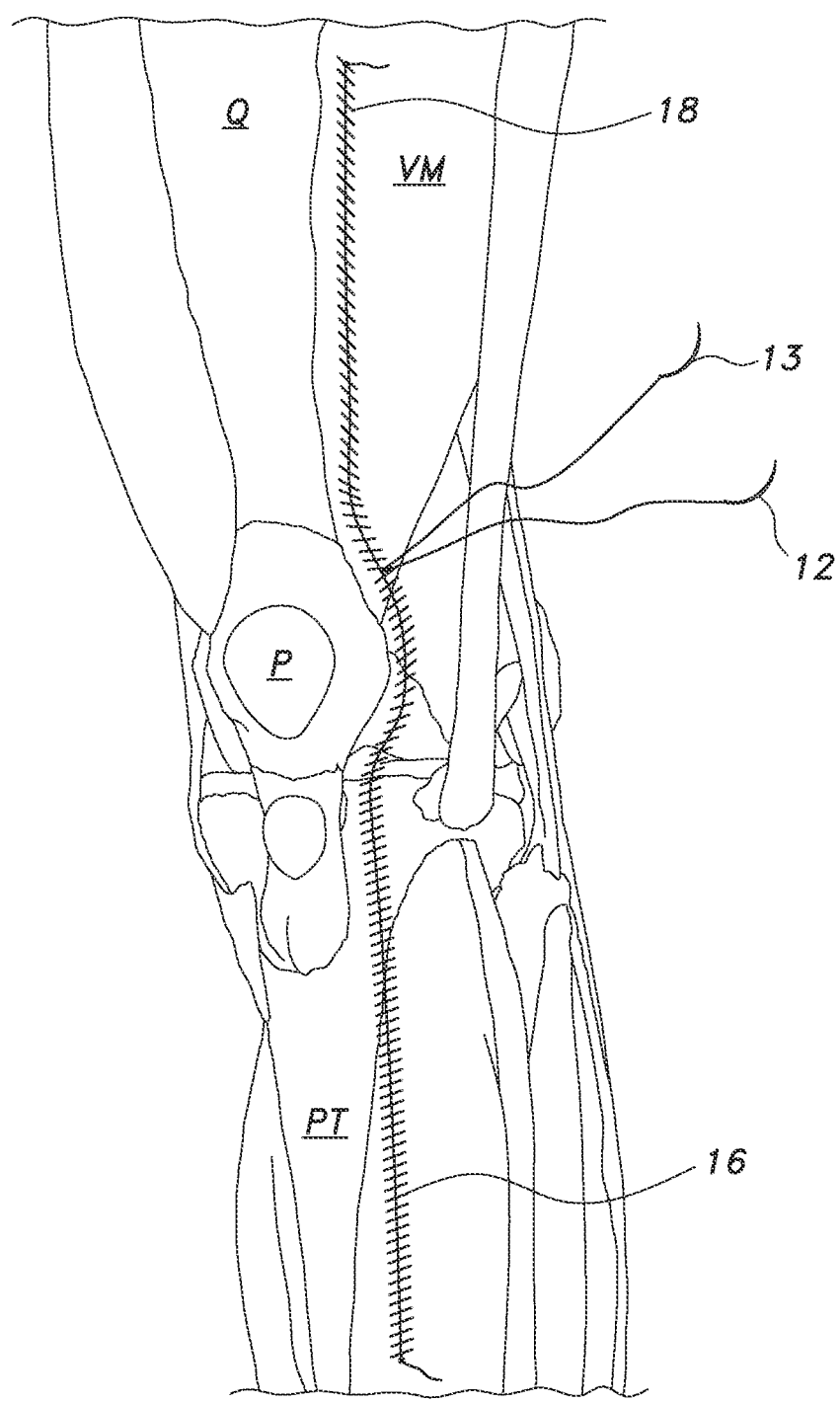
FIG. 5 depicts forming the second series of parallel stitches from the cephalad end to the first point.
Figure 6:
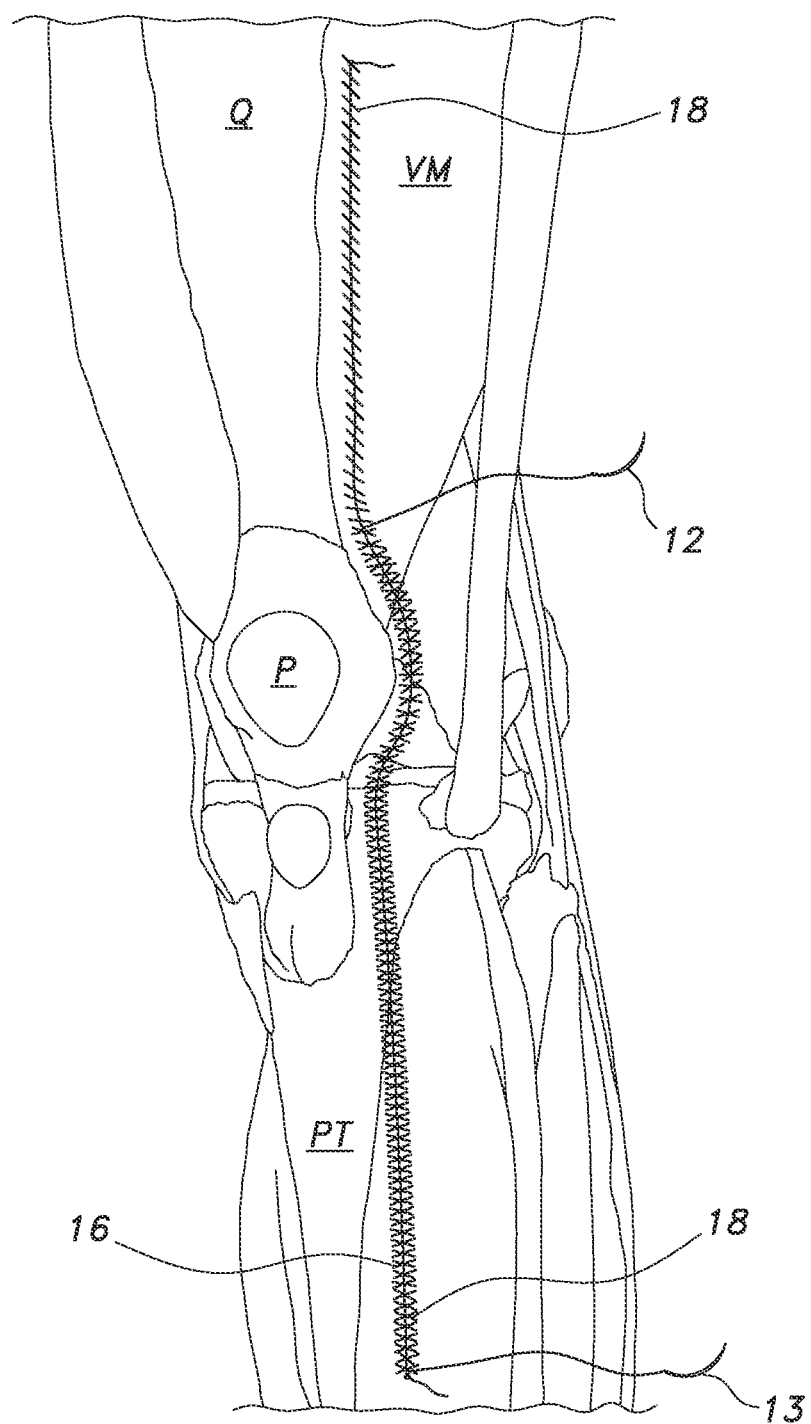
FIG. 6 depicts forming the second series of parallel stitches from the first point to the caudal end of the arthrotomy incision.
Figure 7:
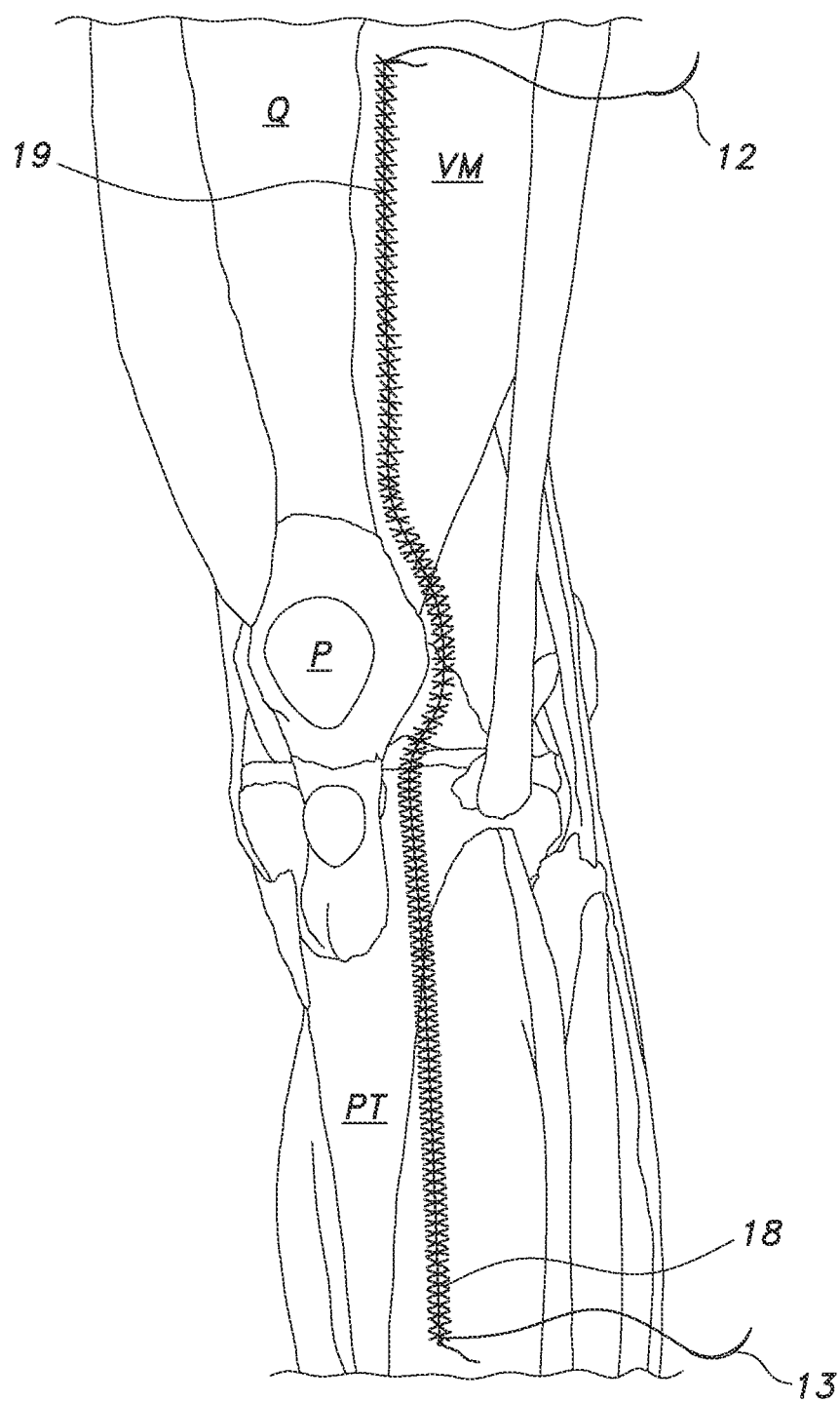
FIG. 7 depicts forming the third series of parallel stitches from the first point to the cephalad end.

Referring to FIGS. 1-7, a method for arthrotomy closure includes closing an arthrotomy incision formed along the quad tendon Q, vastus medialis VM, and patellar tendon PT. The method can include using a first sutured needle 12 to form a first series of parallel stitches 16 from a caudal end of the arthrotomy incision to a first point spaced from the cephalad end of the arthrotomy incision, using a second sutured needle 13 to form a second series of parallel stitches 18 from a cephalad end of the arthrotomy incision to the caudal end of the arthrotomy incision. The second series of stitches 18 intersect the first series of stitches 16 (preferably at an angle of 45 degrees) after passing the first point. After the second series of stitches 18 is formed, the first sutured needle 12 is used to form a third series of stitches 19 from the first point to the caudal end of the arthrotomy incision. The third series of stitches 19 are parallel to the first series of stitches 16 and intersect the second series of stitches 18 (preferably at an angle of 45 degrees). In an embodiment, the first point can be proximate the superior pole of the patella P or slightly beyond the superior pole of the patella P.

In an embodiment, the first sutured needle 12 is positioned at the caudal end of the arthrotomy incision, with the knee positioned in 90 degrees of flexion. The first sutured needle 12 is passed across the caudal most end of the arthrotomy incision. A tail end of the first suture, approximately 1 inch in length, remains spaced from the incision. The suture can be knotted two or three times to maintain the 1-inch tail or first tail 14 and to anchor the suture at the caudal end. The suture can be a vicryl suture (e.g., No. 1 vicryl suture). The one inch long tail left after the suture is tied is not cut short and is later used. A first series of parallel stitches 16 is then formed to about the superior pole of the patella or slightly beyond the superior pole of the patella P. When the first sutured needle reaches the capsule medial to the patella P, the patient can exercise less flexion of the knee (e.g., a flexion of 50 degrees). Less flexion makes repair of the capsule in this region much easier to accomplish. When the capsule repair to the superior pole of the patella P or slightly beyond the superior pole of the patella P is accomplished by the first sutured needle 12, the first sutured needle 12 can be released and the second sutured needle 13 can be used to begin repair of the capsule of the knee at the cephalad end of the arthrotomy.

Before repair from the cephalad end of the arthrotomy begins, it is preferable that the knee is in less than 90 degrees flexion to facilitate passing the anchor stitch. After the anchor stitch is passed, the knee can be at 90 degrees flexion for at least a portion, if not all, of the remainder of the repair. The anchor stitch preferably leaves a tail end of the suture, approximately 1 inch in length, spaced from the incision. In this manner, a second tail 11 is formed. The second suture can be knotted two or three times to maintain the 1-inch tail and to anchor the suture at the cephalad end. The capsule is then repaired by forming a second series of parallel stitches 18 using a running suture technique as was described for repairing the distal half of the capsule. When the capsule has been closed completely, the sutures meet in the middle of the arthrotomy. The repair continues by maintaining the 90 degree flexion position while the second sutured needle 13, anchored at the cephalad end, forms the second series of stitches 18 intersecting the first series of stitches 16 (preferably at an angle of 45 degrees) and passes through the already repaired capsule all the way to the caudal most edge of the arthrotomy. The second suture is then tied to the first tail 14 and the tied suture may be finished by cutting the tail short.

The first sutured needle 12, now positioned at the superior pole of the patella, is then used to form the third series of stitches 19 to the cephalad end while the 90 degree knee flexion position is maintained. The third series of stitches 19 facilitates repair of the VMO fascia back to the quadriceps tendon edge. The stitches of the third series of stitches 19 is preferably no more than 3 mm apart and are parallel to each other. To complete the repair at the cephalad end of the incision, the knee flexion is reduced to approximately 40 or 50 degrees, which facilitates exposure or ability to expose the fascia sufficiently to complete the repair. Once at the cephalad end, the first suture is tied to the second tail 11 and the tied suture may be finished by cutting the tail short.

If the arthrotomy was made through the quadriceps tendon as is commonly done, the first series of stitches is sufficient to repair the quadriceps tendon and the second series of stitches serves as reinforcement. Preferably, the first series of parallel stitches 16, the second series of parallel stitches 18, and the third series of parallel stitches 19 are placed at angle of 45 degrees or about 45 degrees to the capsule arthrotomy incision. Further, while parallel stitches are described, other types of stitches that achieve a watertight seal can be used for the present closure technique.

This repair, properly done, provides a watertight closure which can be checked by injecting saline or other fluid and checking for leaks. Areas found to leak can be reinforced with additional suture.

It is to be understood that the modified intervastus (MIV) arthrotomy closure technique is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for closing an arthrotomy incision, comprising:
    using a first sutured needle to form a first series of parallel stitches beginning from a caudal end of the arthrotomy incision and extending to a first point spaced from the cephalad end of the arthrotomy incision;
    using a second sutured needle to form a second series of parallel stitches beginning from a cephalad end of the arthrotomy incision and extending to the caudal end of the arthrotomy incision, a portion of the second series of parallel stitches intersecting the first series of parallel stitches at a 45 degree angle; and
    after forming the second series of stitches, using the first sutured needle to form a third series of parallel stitches from the first point to the cephalad end of the arthrotomy incision, the third series of parallel stitches being parallel to the first series of parallel stitches and intersecting the second series of parallel stitches at a 45 degree angle.

2. The method for closing an arthrotomy incision according to claim 1, wherein the knee is positioned at 90 degrees of flexion when a first stitch is formed by the first sutured needle at the caudal end of the arthrotomy incision.

3. The method for closing an arthrotomy incision according to claim 2, wherein a first suture tail at the caudal end of the arthrotomy incision is formed after forming the first stitch at the caudal end of the arthrotomy incision.

4. The method for closing an arthrotomy incision according to claim 3, wherein the knee is positioned in less than 90 degrees of flexion when a first stitch is formed by the second sutured needle at the cephalad end of the arthrotomy incision.

5. The method for closing an arthrotomy incision according to claim 4, wherein a second suture tail at the cephalad end of the incision is formed after forming the first stitch at the cephalad end of the incision.

6. The method for closing an arthrotomy incision according to claim 5, wherein a second suture forms the second series of stitches, the second suture is tied to the first tail after the second series of parallel stitches is formed.

7. The method for closing an arthrotomy incision according to claim 6, wherein a first suture forms the first series of stitches, the first suture is tied to the second tail after the third series of parallel stitches is formed.

8. The method for closing an arthrotomy incision according to claim 1, wherein the first series of parallel stitches, the second series of parallel stitches, and the third series of parallel stitches form an angle of 45 degrees with the arthrotomy incision.

9. A method for closing an arthrotomy incision, comprising:
    using a first sutured needle to form a first series of parallel stitches beginning from a caudal end of the arthrotomy incision and extending to a first point spaced from the cephalad end of the arthrotomy incision;
    using a second sutured needle to form a second series of parallel stitches beginning from a cephalad end of the arthrotomy incision and extending to the caudal end of the arthrotomy incision, a portion of the second series of parallel stitches intersecting the first series of parallel stitches at a 45 degree angle; and
    after forming the second series of stitches, using the first sutured needle to form a third series of parallel stitches from the first point to the cephalad end of the arthrotomy incision, the third series of parallel stitches being parallel to the first series of parallel stitches and intersecting the second series of parallel stitches at a 45 degree angle,
    wherein the knee is positioned at 90 degrees of flexion when a first stitch is formed by the first sutured needle at the caudal end of the arthrotomy incision, and
    wherein the knee is positioned in less than 90 degrees of flexion when a first stitch is formed by the second sutured needle at the cephalad end of the arthrotomy incision.

10. The method for closing an arthrotomy incision according to claim 9, wherein a first suture tail at the caudal end of the arthrotomy incision is formed after forming the first stitch at the caudal end of the arthrotomy incision.

11. The method for closing an arthrotomy incision according to claim 9, wherein a second suture tail at the cephalad end of the incision is formed after forming the first stitch at the cephalad end of the incision.

* * * * *